US00PP25372P3

(12) United States Plant Patent
Schoone

(10) Patent No.: US PP25,372 P3
(45) Date of Patent: Mar. 24, 2015

(54) ***PHALAENOPSIS* ORCHID PLANT NAMED 'LULLABY'**

(50) Latin Name: ***Phalaenopsis* hybrid**
Varietal Denomination: Lullaby

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 103 days.

(21) Appl. No.: 13/986,330

(22) Filed: Apr. 22, 2013

(65) Prior Publication Data

US 2013/0291258 P1 Oct. 31, 2013

Related U.S. Application Data

(60) Provisional application No. 61/638,028, filed on Apr. 25, 2012.

(30) Foreign Application Priority Data

Apr. 26, 2012 (NL) ..... PBR OPS908

(51) Int. Cl.
*A01H 5/00* (2006.01)

(52) U.S. Cl.
USPC ..... Plt./311

(58) Field of Classification Search
USPC ..... Plt./311
See application file for complete search history.

*Primary Examiner* — Annette Para
(74) *Attorney, Agent, or Firm* — Foley & Lardner LLP; Sunit Talapatra

(57) ABSTRACT

A new and distinct *Phalaenopsis* plant named 'Lullaby' particularly characterized by flowers which are green/white with red/purple stripes and a purple labellum; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis* hybrid.

Variety denomination: 'Lullaby'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Lullaby'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Lullaby' is a product of a controlled breeding program conducted by the inventor, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Lullaby' originated from a cross made by the inventor in 1999 in Strengweg, Heemskerk, The Netherlands. The female or seed parent is the *Phalaenopsis* cultivar designated 'Salu Spot', unpatented. The male or pollen parent is the *Phalaenopsis* cultivar designated 'Paifang's Auckland', unpatented. The new *Phalaenopsis* 'Lullaby' was discovered and selected by the inventor as a single flowering plant within the progeny of the stated cross in a controlled environment in 2007 in Strengweg, Heemskerk, The Netherlands.

Asexual reproduction of the new *Phalaenopsis* cultivar by tissue culture was first performed in November, 2007 in Cieweg 13, Heemskerk, The Netherlands, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be unique characteristics of 'Lullaby', which in combination distinguish this *Phalaenopsis* as a new and distinct cultivar:

1. flowers which are green/white with red/purple stripes and a purple labellum;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Lullaby', the flowers of the female parent 'Salu Spot' are white with red spots/stripes and the male parent 'Paifang's Auckland' has red colored flowers, whereas the flowers of 'Lullaby' are green/white with red/purple stripes.

Presently, there is no other commercial cultivar to which 'Lullaby' can be meaningfully compared.

BRIEF DESCRIPTION OF THE PHOTOGRAPHS

The accompanying photographs illustrate the overall appearance of the new *Phalaenopsis* 'Lullaby' showing the colors as true as is reasonably possible with colored reproductions of this type. Colors in the photographs may differ slightly from the color values cited in the detailed botanical description, which accurately describe the color of 'Lullaby'.

DETAILED BOTANICAL DESCRIPTION

Figure 1:
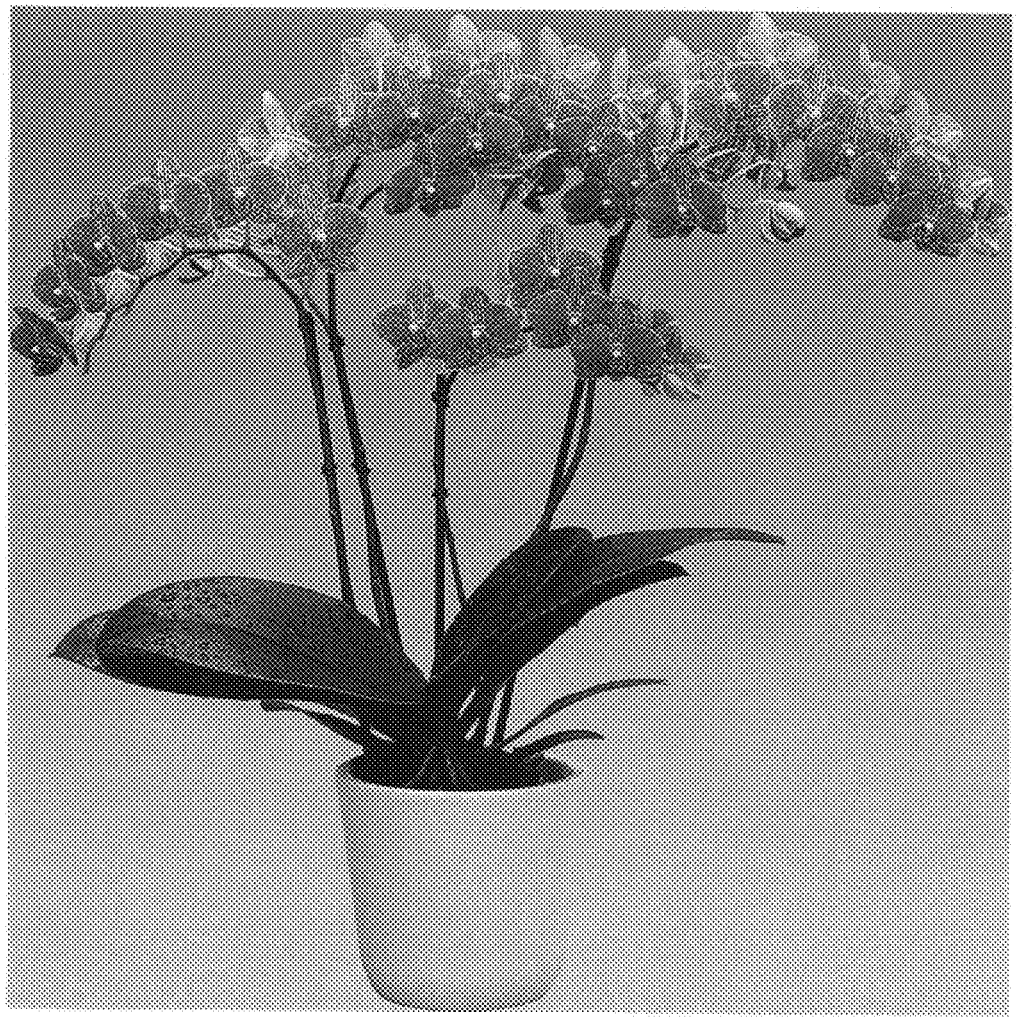
FIG. 1 shows a side view perspective of a typical flowering plant of 'Lullaby' in a 12 cm pot, at 16 months of age.

The new *Phalaenopsis* cultivar 'Lullaby' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Lullaby' as grown in a greenhouse in Strengweg, Heemskerk, The Netherlands, under conditions which closely approximate those generally used in commercial practice. Initially, the ideal temperature to grow plants of 'Lullaby' is 27° C. during the day and at night. Then, during the flowering phase of 'Lullaby', the ideal growing temperature is 20-22° C. during the day and 18° C. at night. Light levels for growing 'Lullaby' are a minimum of 5,000 lux and a maximum of 10,000 lux. A balanced fertilizer with level of 200 ppm N, 87 ppm P, 168 ppm K is applied. Duration of growth of 'Lullaby' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Lullaby' plants described is 12 months after potting.

Classification:

*Botanical.*—*Phalaenopsis* hybrid.

Parentage:

*Female or seed parent.*—*Phalaenopsis* cultivar designated 'Salu Spot', unpatented.

*Male or pollen parent.*—*Phalaenopsis* cultivar designated 'Paifang's Auckland', unpatented.

Propagation:

*Type.*—Tissue culture.

*Rooting habit and description.*—Fleshy; approximately 3 mm-6 mm wide and green in color (RHS 194C); freely branching. It takes 12 weeks for plants growing in tissue culture to initiate roots.

Plant:

*Size at maturity.*—Height: about 50 cm. Spread: about 46 cm.

*Growth habit.*—Small; dark green leaves and a relatively large raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 2 peduncles with flowers appear.

Foliage:

*Quantity per plant.*—About 6 to 8 leaves are produced before flowering.

*Arrangement and attachment.*—Half up/horizontal and on two sides.

*Overall shape of leaf.*—Oval, the tip is little pointy and asymmetric.

*Texture* (*upper* & *underside*).—Smooth and leathery.

*Pubescence.*—3 to 4 Pairs of leaves.

*Mature leaf length.*—About 12 to 18 cm.

*Mature leaf width.*—About 5 to 8 mm.

*Mature leaf thickness.*—About 1.5 mm.

*Mature leaf color.*—Upper side: green (RHS 139B). Under side: yellow/green (RHS 146A).

*Leaf base.*—Acute.

*Margin.*—Entire.

*Venation.*—Pattern: parallel. Color of midvein: upper side: green (RHS 139B). under side: yellow/green (RHS 146B).

Raceme:

*Quantity per plant.*—About 1 to 4.

*Number of flowers per raceme.*—About 8 to 18.

*Length.*—About 28 to 48 cm.

*Diameter.*—About 4 mm.

*Strength.*—Strong.

*Aspect.*—Upright.

*Texture.*—Glabrous and smooth.

*Color.*—Green/yellow (RHS 146A).

*Internode.*—Length: about 25 to 40 mm.

Inflorescence description:

*Appearance.*—Upright to slightly pendant, racemose inflorescence with bilaterally symmetrical flowers that open in succession beginning with the lowermost flower.

*Buds.*—Height (from base to tip): about 15 mm. Diameter (at midpoint): about 14 mm. Shape: egg-shaped. Color: yellow/green (RHS 145A) with on both sides on the large vein yellow/green (RHS N144D). Some other smaller veins are purple (RHS N79A).

*Flowering time.*—For an untreated plant (flowering plant that has not undergone cold-treatment where the plant grows at a temperature of 18° C. to 19° C. for about 4 to 8 weeks after a period of about 30 weeks at a temperature of 25° C.), 2 racemes appear with about 16 to 20 flower buds and flowers per inflorescence. First flowers can be expected approximately 4 to 6 months after planting a plant with a leaf diameter of 3 to 5 cm. Flowers persistent.

*Flowering longevity.*—On the plant: about 4 to 6 months; lastingness of cut flowers: has not been observed.

*Fragrance.*—No fragrance.

Figure 2:
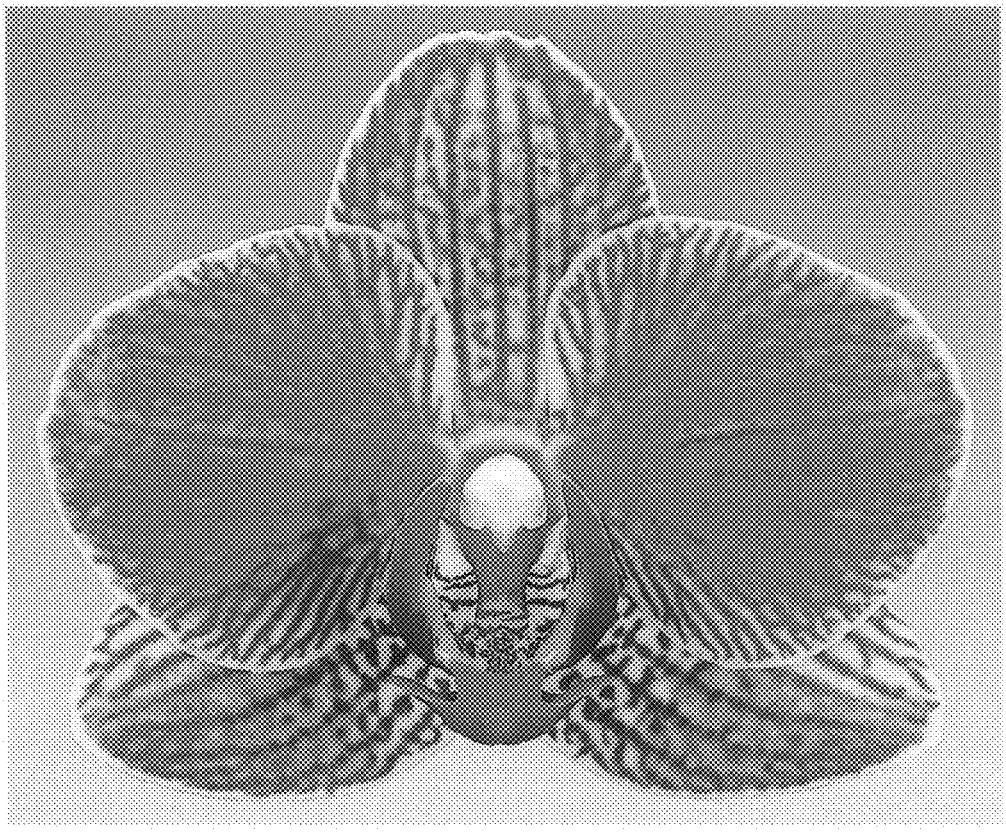
FIG. 2 shows a close-up view of the typical buds and flowers of 'Lullaby'.
Figure 3:
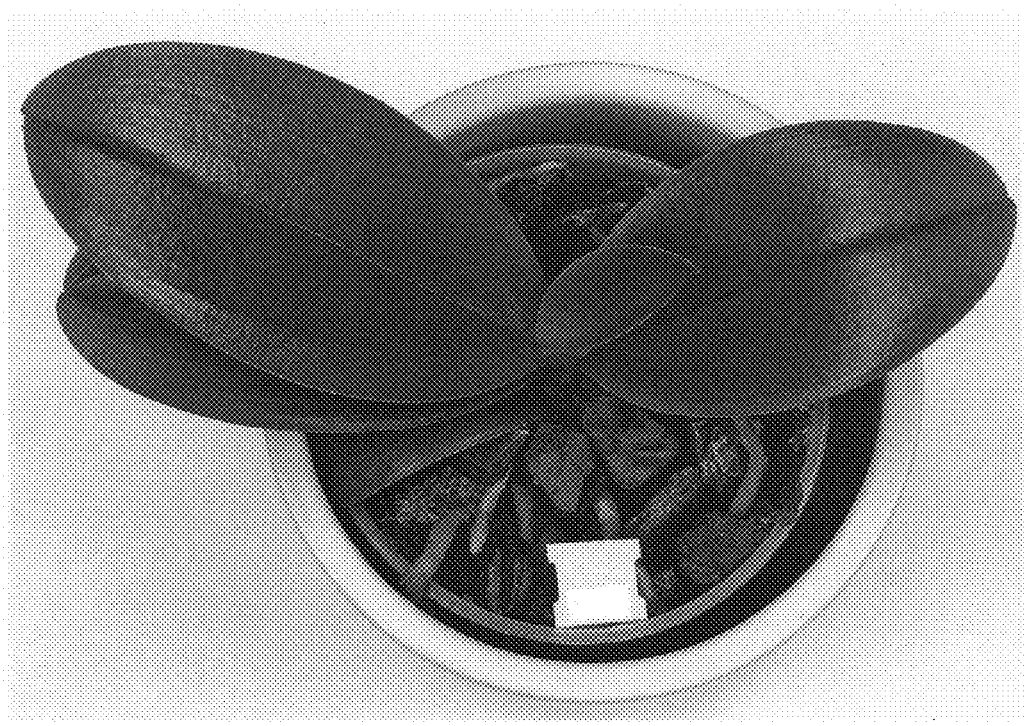
FIG. 3 shows a close-up view of the typical leaves of 'Lullaby'.

*Flower.*—Rate of opening: Flowers fully opened about 2 to 3 days after petal and sepal separation. Orientation at opening: slanted upward and outward. Shape: see FIG. 2. Size: Height: about 33 mm to 40 mm. Diameter: about 43 mm to 50 mm. Depth of tube: about 8 mm.

*Petals.*—Quantity and arrangement: six petals that are trimerous, overlapping and arranged in 2 whorls. Petals are more pronounced than sepals. Arrangement: Inner whorl of petals comprises 3 petals, 2 lateral petals and labellum. 2 lateral petals: Overall shape: broadly ovate, little triangular and weakly cupped. Apex: oval. Margin: entire and weakly undulate. Base: broadly ovate. Length: about 19 mm to 26 mm. Width: about 17 mm to 24 mm. Texture: Upper surface: smooth and satiny. Under surface: smooth and satiny. Color (when fully opened): upper side: green/white (RHS 157A) with many red/purple stripes and spots(RHS N79C). Veins are a bit darker (RHS N79B). Under side: edges are green/white (RHS 157A), rest is red/purple (RHS 71A). In the center from top to bottom green/white (RHS 157A).

*Labellum.*—Overall shape: 3-lobed with 2 prominent callosities at central junction of the lateral lobes and base of the midlobe. Lateral lobes of labellum fold upward about the column; the midlobe extends forward and is terminated by 2 short filiform appendages at the apex. Lateral lobes of the labellum are ovate in shape while the midlobe is triangular with a bump and a rib on it Margin: entire. Apex: oval. Length: about 18 mm. Width (not flattened): about 11 mm. Texture: Upper and under surface: smooth and satiny. Color (when fully opened): Midlobe: upper surface: at the base some yellow (RHS 12A), than large part red/purple (RHS 59A), which runs into purple/violet (RHS N81A). Under side: at base some yellow (RHS 12A) and white (RHS NN155A). In the center white runs from top to bottom. Purple on the edges (RHS 59A), closer to the center it becomes RHS N81A. Lateral lobes: upper surface: at base some yellow (RHS 13A), rest is white (RHS NN155B) with some red/purple stripes and spots (RHS 59A). Also some RHS 59A on the sides and purple (RHS N81A) at the top. Under side: at the base white (RHS NN155B), at the top purple edge (RHs N78A) which runs into red/purple (RHS 9B) on top a little bit of yellow (RHS 12B). Chirri: about 1 mm. color: RHS NN155C and some purple (RHS N81A). Pestle (Callosities): Length: about 3 mm. Width (not flattened): about 3 mm. Color: green/white (RHS 157A) with on top and inside yellow (RHS 12A) with red/purple spots (RHS 59B).

*Sepals.*—Arrangement: Outer whorl comprises 3 sepals. Overall shape: oval and weakly cupped. Margin: entire and weakly undulate. Length: about 23 mm. Width: about 18 mm. Apex: dorsal: oval and weakly undulate; lateral: oval, but slightly pointy. Texture: Upper and under surface: smooth and satiny. Color (when fully opened): upper side: green/white (RHS 157A) with some red/purple (RHS N79C). Veins have red/purple spots and stripes (RHS N79A). Lateral sepals have more green/white at the base (RHS 157A) with purple stripes (RHS N79A). Under side: yellow/green (RHS 145B) with red/purple (RHS 71A). Veins are a bit darker (RHS 59A) and the outer edge is white (RHS 157A).

Reproductive organs:

*Arrangement.*—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column.*—Length: about 9 mm. Diameter: about 4 mm. Color: white (RHS NN155D) and purple (RHS N81B). Pollinia: Quantity: two. Diameter: about 1 mm. Color: yellow/orange (RHS 17A).

*Ovary.*—Length: about 2 mm. Diameter: about 1 mm. Color: RHS NN155D.

*Pedicel.*—Length: about 25 mm to 40 mm. Diameter: about 3 mm. Texture: glabrous and smooth. Color: yellow/green (RHS 145B) which runs into yellow/green (RHS 145D).

Disease/pest resistance/susceptibility: No specific resistance or susceptibility observed Temperature tolerance: Tolerant to a low temperature of about 15° C. and to a high temperature about 30° C.

What is claimed is:

1. A new and distinct *Phalaenopsis* plant named 'Lullaby', as illustrated and described herein.

* * * * *